United States Patent

Baker et al.

[11] Patent Number: 5,906,985
[45] Date of Patent: May 25, 1999

[54] PHARMACEUTICAL COMPOUNDS

[75] Inventors: Stephen Richard Baker, Yateley, United Kingdom; Almudena Rubio Esteban, Madrid, Spain; John Goldsworthy, Basingstoke, United Kingdom; Concepcion Pedregal Tercero, Madrid, Spain

[73] Assignees: Eli Lilly and Company Limited, Basingstoke, United Kingdom; Lilly, S.A., Madrid, Spain

[21] Appl. No.: 08/916,028

[22] Filed: Aug. 21, 1997

[30] Foreign Application Priority Data

Aug. 27, 1996 [GB] United Kingdom ............ 9617822

[51] Int. Cl.$^6$ ................................ A61K 31/66
[52] U.S. Cl. .................. 514/120; 514/381; 514/517; 514/533; 514/547; 514/553; 514/561; 514/562; 548/253; 558/29; 558/169; 562/11; 562/55; 562/443; 562/105; 562/561; 562/571; 560/38; 560/171
[58] Field of Search ............... 562/571, 443, 562/11, 105, 561, 55; 560/171, 38; 548/253; 558/169, 29; 514/120, 381, 517, 533, 547, 561, 562, 553

[56] References Cited

U.S. PATENT DOCUMENTS

| | | | |
|---|---|---|---|
| 4,190,586 | 2/1980 | Metcalf | 260/326.45 |
| 4,902,719 | 2/1990 | Gerhart | 514/564 |

FOREIGN PATENT DOCUMENTS

| | | |
|---|---|---|
| 656345 | 6/1995 | European Pat. Off. . |
| WO 95/15940 | 6/1995 | WIPO . |

*Primary Examiner*—Michael L. Shippen
*Attorney, Agent, or Firm*—Martin A. Hay

[57] ABSTRACT

Pharmaceutical compounds of the formula

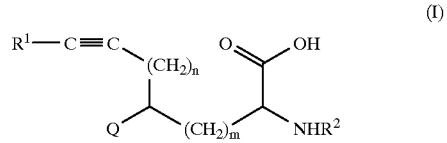

(I)

in which n is 0, 1 or 2 and m is 1 or 2, $R^1$ is hydrogen, $C_{1-10}$ alkyl, $C_{2-10}$ alkenyl, $C_{2-10}$ alkynyl, phenyl, naphthyl, $C_{1-10}$ alkyl-phenyl, $C_{2-10}$ alkenyl-phenyl or $C_{2-10}$ alkynyl-phenyl, said phenyl and naphthyl groups being optionally substituted, $R^2$ is hydrogen or a protecting group, and Q is an acidic group; or a salt or ester thereof.

8 Claims, No Drawings

PHARMACEUTICAL COMPOUNDS

This invention relates to novel chemical compounds and their use as pharmaceuticals.

It is well known that excitatory neurotransmission in the mammalian central nervous system is primarily mediated by the amino acid, L-glutamate, acting on ionotropic and metabotropic receptors, and compounds that modify neurotransmission by interaction with these receptors are of interest for their potential use in the treatment of disorders of the central nervous system.

The compounds of the invention have the formula:

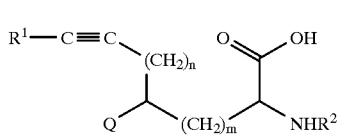

(I)

in which n is 0, 1 or 2 and m is 1 or 2, $R^1$ is hydrogen, $C_{1-10}$ alkyl, $C_{2-10}$ alkenyl, $C_{2-10}$ alkynyl, phenyl, naphthyl, $C_{1-10}$ alkyl-phenyl, $C_{2-10}$ alkenyl-phenyl or $C_{2-10}$ alkynyl-phenyl, said phenyl and naphthyl groups being optionally substituted, $R^2$ is hydrogen or a protecting group, and Q is an acidic group; and salts and esters thereof.

The compounds of the invention (those in which $R^2$ is hydrogen) have been found to be active in tests indicative of their use in the treatment of disorders of the central nervous system such as neurological diseases, for example, neurodegenerative diseases, and as antipsychotic, anticonvulsant, analgesic and anti-emetic agents.

When $R^1$ is $C_{1-10}$ alkyl, it can be straight or branched chain, such as, for example, methyl, ethyl, propyl, isopropyl, butyl and isobutyl. A $C_{2-10}$ alkenyl groups includes, for example, vinyl, prop-2-enyl, but-3-enyl, pent-4-enyl and oct-7-enyl. An alkenyl group can contain more than one double bond and can contain, in addition, one or more triple bonds. A preferred alkenyl group is of the formula R—CH=CH— where R is $C_{1-4}$ alkyl. A $C_{2-10}$ alkynyl group includes, for example, prop-2-ynyl, but-3-ynyl, pent-4-ynyl and oct-7-ynyl. An alkynyl group can contain more than one triple bond and can contain, in addition, one or more double bond. A preferred alkynyl group is of the formula R—C≡C— where R is $C_{1-4}$ alkyl.

The group $R^1$ is preferably hydrogen, $C_{1-4}$ alkyl or optionally substituted phenyl. Preferably n is 1, and m is also preferably 1.

In the above Formula (I), an optionally substituted phenyl or naphthyl group is optionally substituted with, for example, one or more substituents selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino, $C_{1-4}$ acylamino and $C_{1-4}$ alkylthio. A naphthyl group can be 1-naphthyl or 2-naphthyl. When substituted, a phenyl or naphthyl group is preferably substituted by one to three substituents.

When $R^2$ is a protecting group it can be any conventional amino protecting group such as, for example, described in standard textbooks, for instance, T. W. Greene in chapter 7 of Protective Groups in Organic Synthesis, John Wiley and Sons, New York, 1981, and by J. W. Barton in chapter 2 of Protective Groups in Organic Chemistry, J. F. W. McOmie, ed., Plenum Press, New York, 1973. Examples of such groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred nitrogen protecting groups are benzyl (—$CH_2C_6H_5$), acyl [C(O)R] or $SiR_3$ where R is $C_{1-4}$ alkyl, halomethyl, or 2-halo-substituted-($C_{2-4}$ alkoxy).

The group Q in the above Formula (I) is an acidic group, and examples of Q include $CO_2H$, tetrazolyl, $PO_3H$, $OPO_3H_2$, $PO_2H$, $OPO_2H$, $SO_3H$, $OSO_3H$ and CONHOH, Q being most preferably $CO_2H$.

A preferred group of compounds of Formula (I) is one of the following formula:

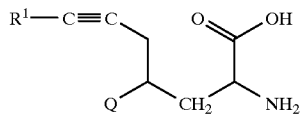

in which $R^1$ is hydrogen, $C_{1-4}$ alkyl or optionally substituted phenyl, and Q is COOH, or a salt or ester thereof.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention contain asymmetric carbon atoms as indicated by the asterisks in Formula (I), and this gives rise to diastereoisomers. The compounds can be prepared as racemates or as enantiomers, and individual enantiomers can be isolated from racemates by conventional techniques if so desired. Such racemates and individual enantiomers, RR, RS, SR, SS, form part of the present invention. Preferred enantiomers are those of the formula:

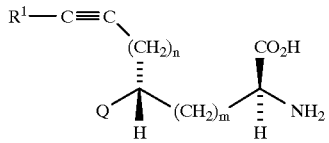

and in the most preferred instance when m is 1 and n is 1, these compounds have the configuration 2S,4R.

The invention also comprises a process for producing a compound of Formula (I) above, which comprises:

1) hydrolysing a compound of the formula:

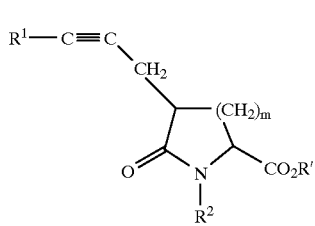

(III)

in which $R^1$ has the values given above, and R' and $R^2$ are protecting groups, to give a compound of Formula (I) in which n is 1 and Q is $CO_2H$, 2) oxidising a compound of the formula:

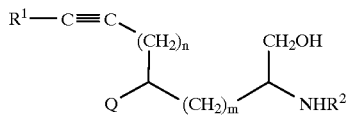

(IV)

in which $R^1$, $R^2$ and n have the values given above, and $R^2$ is a protecting group, or 3) reacting a compound of the formula:

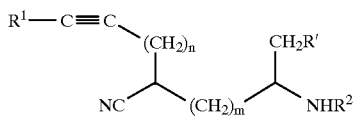

(V)

in which $R^1$ and n have the values given above, with azide, to give a compound of Formula (I) in which Q is tetrazoyl.

The reaction described in process variant (1), above, is one of hydrolysis under conventional hydrolysis conditions using acid or base. It is preferred to use acid. For example, the reaction can be carried out in aqueous medium and in the presence of acid such as, for example, hydrochloric acid, preferably at a temperature of from 100° C. to 120° C.

Intermediate compounds of Formula (III) can be prepared by reacting a compound of the formula:

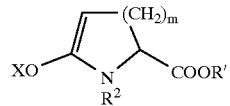

(VI)

in which X is a metal atom, with an alkylating reagent of the formula:

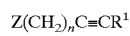

(VII)

where Z is a leaving group such as halo, preferably chloro or bromo, or mesylate or tosylate. Compounds of Formula (VI) can, in their turn, be prepared by reacting the appropriate compound of the formula:

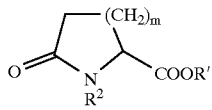

(VIII)

such compounds being readily prepared by known methods, with a metallic reagent preferably lithium hexamethyldisilazide (LiHMDS). It is not essential to separate the metal salt from the reaction medium before carrying out the alkylation reaction. Such reactions are preferably carried out in an inert organic solvent, such as, for example, tetrahydrofuran, and at a temperature of −100° C. to −50° C.

The alkylation reaction can give rise to a mixture of isomers and the intermediate needed for the preparation of the preferred compounds of the invention can be separated by conventional physical means such as chromatography.

The reaction of process variant (2) is preferably carried out in an organic solvent such as, for example, tetrahydrofuran, at a temperature of −50° C. to −100° C.

The intermediates of Formula (IV) can readily be prepared from known compounds. For example, they can be prepared by ring opening the appropriate oxazolidine of the formula:

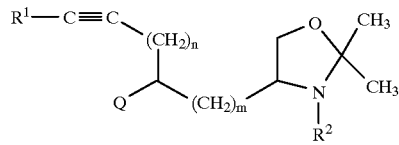

(IX)

In the above reactions it is frequently necessary to protect the nitrogen atom by means of a protecting group, preferably a carboxy protecting group such as BOC, which can readily be removed when the reaction is completed. Similarly a carboxy group may be protected by conventional groups such as $C_{1-4}$ alkyl.

Compounds of Formula (IX) can be prepared by reaction of a suitable alkylating agent with a compound of the formula:

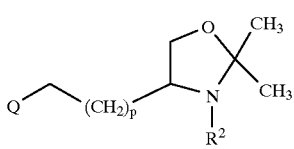

(X)

prepared by reducing the corresponding unsaturated compound of formula:

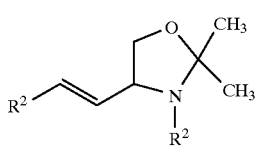

(XI)

derived from the aldehyde:

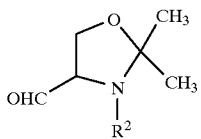

(XII)

Compounds of Formula (XI) and (XII) are known in the art.

With regard to process variant (3), the conversion of nitrile to tetrazolyl (5-tetrazolyl) is preferably carried out employing tributyltin azide, or an alkali metal azide and ammonium chloride or triethylamine hydrochloride, in an organic solvent such as dimethylformamide, and preferably at a temperature of from 80° C. to 150° C. The compounds of Formula (V) can be prepared from the prior art compound of Formula (XII) above by reaction of appropriate yield to give a compound of the formula:

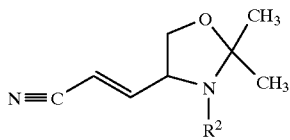

followed by hydrogenation, alkylation and hydrolysing to open the oxazolidine ring.

The compounds described above have pharmaceutical activity. They have been shown to possess affinity for ionotropic glutamate receptors.

Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-asparate, AMPA, and kainate (Sommer B. and Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. and Conn J. P., Trends Pharmacol. Sci. 14: 13–20, 1993).

The affinity of the compounds of the invention for ionotropic. glutamate receptors has been demonstrated by the selective displacement of $^3$H- kainate binding to membranes obtained from human embryonic kidney (HEK) 293 cells stably transfected with the ionotropic glutamate receptor sub-types GluR 5 (Korczak et al. (1995) Receptors and Channels 3: 41–49) or GluR 6 (Hoo et al. (1994) Receptors and Channels 2: 327–337). In the former test compounds of the invention had a Ki of 0.5 µM or less. Functional activity at either GluR 5 or 6 glutamate receptors was determined using whole cell voltage clamp electrophysiology.

Compound selectivity was evaluated using radioligand binding studies and whole cell voltage patch clamp electrophysiology using AMPA ionotropic glutamate receptors expressed in HEK 293 cells (GluR 1, 2, 4 [$^3$H] AMPA binding). In addition activity at rat GluR 5 receptors and AMPA receptors was established using preparations of acutely isolated dorsal root ganglion neurons and cerebellar Purkinje cells, respectively.

The compounds of the invention are thus indicated for use in the treatment of neurological disorders such as acute neurodegenerative diseases, for example stroke, cerebral ischemia and head and spinal cord trauma, and chronic neurodegenerative diseases such as, for example, Alzheimer's disease, Parkinson's disease, amyotrophic lateral sclerosis, AIDS-induced dementia and Huntington's Chorea. The compounds are also indicated for use as antipsychotic, anticonvulsant, analgesic and anti-emetic agents. They are also of potential use as anxiolytic and antidepressant agents.

The invention also includes a pharmaceutical composition comprising a pharmaceutically-acceptable diluent or carrier in association with a compound of Formula (I), or a pharmaceutically-acceptable salt thereof.

The compounds may be administered by various routes, for example, by the oral or rectal route, topically or parentally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

(2S,4R)-2-Amino-4-(but-2-yn-1-yl)pentanedioic acid

1) To a mixture of 2-butyn-1-ol (6.30 g, 90 mmol) and pyridine (0.5 ml) in dry diethyl ether (25 ml), under positive nitrogen pressure, and cooled to −40° C. in a dry ice/acetonitrile bath, was added, dropwise, phosphorus tribromide (7.38 g, 32 mmol). The reaction mixture was then stirred for 2 hours at −40° C. before being allowed to warm to ambient temperature. Finally the reaction mixture was heated under reflux for 30 minutes.

The reaction mixture was allowed to cool before being poured into saturated sodium chloride solution (50 ml). After separation of the ether layer, the aqueous phase was extracted twice with diethyl ether, and the combined ethereal phase dried over magnesium sulphate, filtered and evaporated in vacuo to give an amber oil. The crude oil was distilled on a Kugelrohr bulb to bulb apparatus to give 1-bromo-2-butyne as a clear, mobile.

ii) To a solution of (2S)-benzyl-N-(t·butoxycarbonyl) pyroglutamate (7.20 g, 22 mmol) in dry tetrahydrofuran (70 ml) under positive nitrogen pressure, and cooled to −78° C. in a dry ice/acetone bath, was added lithium bis(trimethylsilyl)amide (25 ml of IM THF solution, 25 mmol). After stirring at −78° C. for 1 hour, the reaction mixture was rapidly cannulated under nitrogen pressure to a solution of 1-bromo-2-butyne (6.00 g, 44 mmol) in dry tetrahydrofuran (20 ml), also under positive nitrogen pressure at −78° C. The resulting mixture was then stirred at −78° C. for 2 hours.

The reaction mixture was quenched at −78° C. with saturated ammonium chloride solution and then extracted three times with diethyl ether. The combined ethereal extracts were dried over magnesium sulphate, filtered and evaporated in vacuo to give an oil. The crude oil was purified by flash chromatography on silica (eluent hexane: diethyl ether=2:1) to give (2S,4R)benzyl-N(t·butoxycarbonyl)-4-(but-2yn-1-yl)pyroglutamate as a white solid.

iii) To a solution of (2S,4R)benzyl-N(t·butoxycarbonyl)-4-(but-2-yn-1-yl)pyroglutamate (400 mg, 1.1 mmol) in tetrahydrofuran (10 ml) was added 1 molar lithium hydroxide (3.3 ml, 3.3 mmol) and the mixture stirred at ambient temperature for 16 hours.

The reaction mixture was acidified to pH2 with 1 molar hydrochloric acid and extracted three times with diethyl ether. The combined ethereal extracts were dried over magnesium sulphate, filtered and evaporated in vacuo to give (2S,4R)-2-(t·butoxycarbonylamino)-4-(but-2-yn-1-yl) pentanedioic acid as a viscous oil.

iv) To a solution of (2S,4R)-2-(t·butoxycarbonylamino)-4-(but-2-yn-1-yl)pentanedioic acid (400 mg) in moist diethyl ether (10 ml) was added, with ice-bath cooling, trifluoroacetic acid(4 ml). The reaction mixture was then stirred at ambient temperature for 4 hours.

The reaction mixture was evaporated to dryness in vacuo, redissolved in water and azeotroped to remove excess trifluoroacetic acid. The resulting white solid was purified by cation-exchange chromatography (Dowex 50×8–100). The column was eluted sequentially with water, water:THF 1:1 and water again, and the amino acid was finally eluted with water:pyridine 9:1. The pyridine was removed in vacuo and the residual solid redissolved in water and freeze-dried to give the title compound as a fluffy white solid, m.p. 120° C. (softens).

EXAMPLE 2

(2S,4R)-2-Amino-4-(pent-2-yn-1-yl)pentanedioic acid i) 1-bromo-2-pentyne prepared by the method of Example 1(i).

ii) (2S,4R)-benzyl-N-(t·butoxycarbonyl)-4-(pent-2-yn-1-yl)pyroglutamate, prepared by the method of Example 1(ii).

iii) (2S,4R)-2(t·butoxycarbonylamino)-4-(pent-2-yn-1-yl) pentanedioic acid, prepared by the method of Example 1(iii).

iv) (2S,4R)-2-amino-4-(pent-2-yn-1-yl)pentanedioic acid, prepared by the method of Example 1(iv) to give a white solid, m.p. 198°–200° C. (dec.)

EXAMPLE 3

(2S,4R)-2-Amino-4-(hex-2-yn-1-yl)pentanedioic acid i) 1-bromo-2-hexyne, prepared by the method of Example 1(i).

ii) (2S,4R)-benzyl-N-(t·butoxycarbonyl)-4-(hex-2-yn-1-yl)pyroglutamate, prepared by the method of Example 1(ii).

iii) (2S,4R)-2-(t·butoxycarbonylamino)-4-(hex-2-yn-1-yl)pentanedioic acid, prepared by the method of Example 1(iii).

iv) (2S,4R)-2-amino-4-(hex-2-yn-1-yl)pentanedioic acid, prepared by the method of Example 1(iv) to give a white solid, m.p. 200°–201° C.

EXAMPLE 4 i) (2S,4R)-1-(tert·butoxycarbonyl-4-(pron-2-ynyl)benzyl pyroalutamate

To a solution of benzyl N-tert·butoxycarbonyl pyroglutamate (2 g, 6.26 mmol) in dry tetrahydrofuran (30 ml) under argon was added a 1M solution of lithium hexamethyldisilazide in dry tetrahydrofuran (7.5 ml, 7.5 mmol) at −78° C. After one hour, this solution was cannulated to a previously prepared solution of prop-2-ynyl bromide (2.98 g, 25 mmol) in 20 ml dry tetrahydrofuran, and stirring was continued for two hours. The reaction mixture was quenched with saturated ammonium chloride solution, and extracted with dichloromethane. The organic phase was dried over anhydrous sodium sulfate, filtered and evaporated to dryness. The diastereomeric mixture was evaporated by flash column chromatography using ethyl acetate/hexane (1:3) as eluent.

The title compound was separated, m.p. 102°–103° C.

ii) (2S,4R)-2-(tert·butoxycarbonylamino)-4-(prop-2-ynyl)pentanedioic acid

To a solution of the pyroglutamate (200 mg) in tetrahydrofuran (5 ml) was added a 2.5 N aqueous solution of LiOH (4 ml). The mixture was stirred at room temperature for 4 hours. After this time the THF was evaporated and the residue extracted with ethylic ether to remove benzyl alcohol. The aqueous layer was acidified to pH=2 with 12 N HCl in an ice-bath. Then extracted with ether, dried over anhydrous sodium sulfate and the solvent evaporated to dryness.

iii) (2S,4R)-2-(amino)-4-(prop-2-ynyl)pentanedioic acid

The residue obtained in the previous reaction was stirred for 4 hours with a 1 N solution of HCl in dry ethyl acetate. It was then evaporated to dryness and triturated with ether several times and evaporated under vacuum to remove the volatiles (the bath should be cold). When the HCl salt was obtained as a solid methanol and propylene oxide was added and subsequently evaporated and the process repeated several times until a solid was obtained, then the solid was filtered off, and triturated with ether, to give the title compound, m.p. 164°–165° C.

EXAMPLE 5 i) (2S,4R)-1-(tert·butoxycarbonyl-4-(3-phenylprop-2-ynyl)benzyl prroglutamate

To a mixture of iodobenzene (0.37 ml, 3.36 mmol) and the pyroglutamate (1 g, 2.80 mmol) in triethylamine (15 ml) was added bis-triphenylphosphine palladium dichloride (100 mg, 5%) and copper iodide (33 mg, 2.5%). The reaction mixture was heated at 70°–C. under nitrogen atmosphere for 2.5 hours. After this time the solvent was evaporated and the residue chromatographed using ethyl acetate/hexane (1:4) as eluent to yield an oil.

ii) (2S,4R)-2-(tert·butoxvcarbonylamino)-4-(3-phenylprop-2-ynyl)pentanedioic acid Prepared as described in Example 4(ii).

iii) ($^2$S,$^4$R)-$^2$-(amino)-4-(3-phenylprop-2-ynyl)pentanedioic acid

Prepared as described in Example 4(iii).

The title compound m.p. 164°–166° C.

EXAMPLE 6

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 7

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

We claim:

1. A compound of the formula $$R^1-C\equiv C\diagdown_{(CH_2)_n}\diagup\diagdown_Q\diagup(CH_2)_m\diagdown_{NHR^2}\diagup\diagup^{O}\diagdown OH \quad (I)$$

in which n is 0, 1 or 2 and m is 1 or 2, $R^1$ is hydrogen, $C_{1-10}$ alkyl, $C_{2-10}$ alkenyl, $C_{2-10}$ alkynyl, phenyl, naphthyl, $C_{1-10}$ alkyl-phenyl, $C_{2-10}$ alkenyl-phenyl or $C_{2-10}$ alkynyl-phenyl, said phenyl and naphthyl groups being optionally substituted with one or more substituents selected from $C_{1-4}$ alkyl, $C_{1-4}$ alkoxy, carboxy, hydroxy, cyano, halo, trifluoromethyl, nitro, amino, $C_{1-4}$ acylamino and $C_{1-4}$ alkylthio, $R^2$ is hydrogen or a protecting group, and Q is an acidic group selected from $CO_2H$, tetrazolyl, $PO_3H$, $OPO_3H_2$, $PO_2H$, $OPO_2H$, $SO_3H$, $OSO_3H$ and CONHOH; or a salt or ester thereof.

2. A compound according to claim 1 in which $R^2$ is hydrogen, and $R^1$ is hydrogen, $C_{1-4}$ alkyl or optionally substituted phenyl.

3. A compound according to claim 2 in which n and m are both 1.

4. A compound according to claim 3 in which Q is $CO_2H$.

5. A pharmaceutical formulation comprising a compound according to claim 2, or a pharmaceutically-acceptable salt or ester thereof, together with a pharmaceutically-acceptable diluent or carrier thereof.

6. A method of treating a human suffering from or susceptible to a disease of the central nervous system, which comprises administering to the human an effective amount of a compound according to claim 2.

7. A compound according to claim 2, which is of the formula $$R^1-C\equiv C\diagdown_{(CH_2)_n}\diagdown_{H}\diagdown(CH_2)_m\diagdown_{H}\diagdown_{NH_2}\diagup^{CO_2H}$$

8. A compound according to claim 7, which is selected from:
(2S,4R)-2-Amino-4-(but-2-yn-1-yl)pentanedioic acid,
(2S,4R)-2-Amino-4-(pent-2-yn-1-yl)pentanedioic acid,
(2S,4R)-2-Amino-4-(hex-2-yn-1-yl)pentanedioic acid,
(2S,4R)-2-(amino)-4-(prop-2-ynyl)pentanedioic acid, and
(2S,4R)-2-(amino)-4-(3-phenylprop-2-ynyl)pentanedioic acid.

* * * * *